United States Patent [19]
Ahlbäumer

[11] Patent Number: 5,778,563
[45] Date of Patent: Jul. 14, 1998

[54] SHOE, IN PARTICULAR SPORT SHOE OR ORTHOPAEDIC STOCKING WITH ANKLE STABILIZATION

[76] Inventor: Georg Ahlbäumer, Via Arona 34 (Klinik Gut), CH-7500 St. Moritz, Switzerland

[21] Appl. No.: 698,839

[22] Filed: Aug. 16, 1996

Related U.S. Application Data

[63] Continuation of PCT/EP95/00396 Feb. 3, 1995.

[30] Foreign Application Priority Data

Feb. 16, 1994 [DE] Germany ............... 44 04 911.0

[51] Int. Cl.⁶ ............... A43B 7/14; A43B 7/20; A61F 13/00
[52] U.S. Cl. ............... 36/88; 36/89; 36/140; 602/27; 602/65
[58] Field of Search ............... 36/88, 89, 132, 36/140; 602/27, 65, 66

[56] References Cited

U.S. PATENT DOCUMENTS

| | | | |
|---|---|---|---|
| 1,205,206 | 11/1916 | Hofmeister | 36/89 |
| 2,972,822 | 2/1961 | Tanner | 36/89 |
| 2,994,322 | 8/1961 | Cullen et al. | 602/27 |
| 3,298,365 | 1/1967 | Lewis | 602/27 |
| 3,303,584 | 2/1967 | Werner et al. | |
| 3,494,054 | 2/1970 | Lange | |
| 3,834,377 | 9/1974 | Lebold | 36/89 |
| 4,107,856 | 8/1978 | Bourque | |
| 4,510,927 | 4/1985 | Peters | 602/27 |
| 4,719,926 | 1/1988 | Nelson | 36/89 |
| 4,834,078 | 5/1989 | Biedermann | 602/27 |
| 5,038,762 | 8/1991 | Hess et al. | 602/27 |
| 5,056,509 | 10/1991 | Swearington | 36/89 |
| 5,177,884 | 1/1993 | Rullier | |
| 5,185,000 | 2/1993 | Brandt et al. | 602/65 |
| 5,242,379 | 9/1993 | Harris et al. | 602/27 |
| 5,317,820 | 6/1994 | Bell et al. | 36/89 |
| 5,366,439 | 11/1994 | Peters | 602/27 |
| 5,498,033 | 3/1996 | Hoshizaki et al. | 36/89 |

FOREIGN PATENT DOCUMENTS

| | | |
|---|---|---|
| 385636 | 4/1988 | Austria . |
| 387893 | 3/1989 | Austria . |
| 0356400 | 2/1990 | European Pat. Off. . |
| 0471955 | 2/1992 | European Pat. Off. . |

(List continued on next page.)

OTHER PUBLICATIONS

Kapandji, I.A., Funktionelle Anatomie Der Gelenke, Schematisierte und Kommentierte Zeichnungen zur menschlichen Biomechanik, published by Ferdinand Enke Verlag, pp. 149 to 204 (1985, 1992).

*Primary Examiner*—M. D. Patterson
*Attorney, Agent, or Firm*—Anderson, Kill & Olick, P.C.

[57] ABSTRACT

In a shoe, in particular a sports shoe, with a reinforcement which partially or entirely encloses the foot below the ankle joints and which extends above the upper ankle joint on one or both sides of the foot, wherein the reinforcement has a stirrup element which at least partially surrounds the foot below the ankle joints and a sleeve element which at least partially surrounds the calf above the upper ankle joint, and wherein the sleeve element is connected with the stirrup element on the inner side of the foot and/or on the outer side of the foot via an articulation in order to transmit at least tractive forces between the stirrup element and the sleeve element, it is proposed that the articulation on the outer side of the foot is arranged so as to be offset toward the front in the longitudinal direction of the shoe relative to a center position between the outer malleolus and the inner malleolus of the upper ankle joint and that the articulation on the inner side of the foot is arranged so as to be offset toward the rear in the longitudinal direction of the shoe relative to the center position. In this way, reliable protection against injury is achieved along with sufficient mobility. The reinforcement according to the invention can also be used in connection with an orthopedic stocking or the like textile support fabrics for the stabilization of ankle joints.

83 Claims, 9 Drawing Sheets

FOREIGN PATENT DOCUMENTS

| | | |
|---|---|---|
| 2651416 | 3/1991 | France . |
| 6608312 | 7/1971 | Germany . |
| 3226969 | 11/1983 | Germany . |
| 3520746 | 12/1986 | Germany . |
| 8702913 | 7/1987 | Germany . |
| 3626871 | 8/1987 | Germany . |
| 3626872 | 11/1987 | Germany . |
| 8807537 | 9/1988 | Germany . |
| 8814157 | 2/1989 | Germany . |
| 9307688 | 9/1993 | Germany . |
| 1018526 | 12/1991 | WIPO .................................. 36/89 |
| 3006797 | 4/1993 | WIPO .................................. 602/27 | ns
SHOE, IN PARTICULAR SPORT SHOE OR ORTHOPAEDIC STOCKING WITH ANKLE STABILIZATION

This application is a continuation of a PCT application No. PCT/EP95/00396 filed Feb. 3, 1995 and naming U.S. as a designated state.

The invention is directed to a shoe, especially a sports shoe or orthopedic stocking, with ankle joint stabilization, with a reinforcement which partially or entirely encloses the foot below the ankle joints and which extends above the upper ankle joint on one or both sides of the foot. The reinforcement has a stirrup element which at least partially surrounds the foot below the ankle joints and a sleeve element which at least partially surrounds the calf above the upper ankle joint. The sleeve element is connected with the stirrup element on the inner side of the foot and/or on the outer side of the foot via an articulation in order to transmit at least tractive forces between the stirrup element and the sleeve element.

A cross-country shoe having these features is known from EP 0416437 B1. In order to guide the ski reliably, the sleeve element is connected, via an articulation, with laterally raised tabs of the rear heel shell so that corresponding ski-guiding forces can be transmitted into the calf while relieving the ankle joints. Both articulations have the same height y roughly corresponding to the height of the malleoli and the same distance x from the rear end of the shoe (FIG. 6) so that the straight line connecting the two articulations extends parallel to the transverse axis of the shoe running vertical to the longitudinal axis of the shoe. The two articulations enable extension and flexion as is required in cross-country skiing.

German Utility Model DE 88 07 537 U1 shows a cross-country shoe in which a sleeve which only reaches to the malleolus is connected with a lateral outsole arch at the outside of the shoe and at the inner side of the shoe via articulations which are located correspondingly lower down so as to ensure sufficient flexion-extension mobility for classic cross-country skiing and simultaneously to provide the malleolus with adequate support in the lateral direction for skating technique.

The object of the present invention is to provide a shoe of the type mentioned above, in particular a sports shoe, which protects against ankle injuries, especially injury of the upper ankle joint.

This object is met in that the articulation on the outer side of the foot is arranged so as to be offset toward the front in the longitudinal direction of the shoe relative to a center position between the lateral or outer malleolus and the medial or inner malleolus of the upper ankle joint and in that the articulation on the inner side of the foot is arranged so as to be offset toward the rear in the longitudinal direction of the shoe relative to the center position.

In the prior art the articulation on the outer side of the foot and the articulation on the inner side of the foot lie on a transverse axis (at right angles to the longitudinal direction of the shoe) substantially passing through the center position. In the present invention the articulation on the outer side of the foot is offset toward the front and the articulation at the inner side of the foot is offset toward the rear. Consequently, during a supinating movement of the foot, especially an inverting movement, forces are increasingly transmitted via the articulation on the outer side of the foot from the sole of the foot to the sleeve element and accordingly to the calf with a corresponding braking and limiting of further supination or inversion of the foot. In this way, supination injuries, particularly torn ligaments (fibular ligaments, especially the anterior talofibular ligament) and, even more, skeletal damage (bone injuries, particularly fractures of the malleolus) can be effectively prevented. Similarly, the articulation on the inner side of the foot which is offset toward the rear reduces the risk of pronating injuries or everting injuries, especially fractures of the outer malleolus. The orientation, according to the invention, of the straight connecting line between the articulation on the outer side of the foot and the articulation on the inner side of the foot in relation to the transverse axis is accordingly opposite to that of Henke's axis which characterizes the movements of the tarsal bones below the superior ankle joint. The Henke axis extends diagonally from the bottom rear laterally to the top front medially and, together with the approximately transverse axis of the upper ankle joint, forms a kind of heterogeneous universal joint. The foot also rotates about the Henke axis, at least with more pronounced inverting or everting movements, but not around the (differently oriented) straight connecting line between the articulations of the shoe. Owing to the basic elasticity of the shoe, an inverting or everting movement of the foot is possible initially in spite of the different orientation of the movement axes of the foot and shoe. However, this movement is increasingly inhibited by the shoe.

For this reason, the protection of the talofibular anterior ligament during an inverting movement is particularly effective according to the invention, since this ligament is located anterior to the outer malleolus in the longitudinal direction of the shoe, i.e., approximately at the location of the outer articulation according to the invention which can directly absorb corresponding tractive forces to relieve the loading of the anterior talofibular ligament. The invention intentionally does not strive for the full mobility of the foot within the shoe according to the invention so that foot injuries can be ruled out as far as possible. Nevertheless, as has been shown, an adequate basic mobility is provided since the shoe possesses a certain flexibility and elasticity. At the same time, the stirrup element and the sleeve element must also be constructed so as to be sufficiently rigid against traction so as to effectively limit the inverting movement and everting movement of the foot. The load-relieving forces are transmitted from the calf, via the sleeve element, the articulation and the stirrup element, to the plantar side of the foot while bypassing the upper and lower ankle joint. No problems arise in this transmission of force since the body weight loads the stirrup element which at least partially encloses the foot and is constructed, if necessary, in one piece with a sole of the shoe.

In a particularly preferred embodiment form of the invention, a momentary slipping of the sole of the foot is prevented in that the stirrup element completely surrounds the foot and is connected with the sleeve element acting at the calf via the articulation on the outer side of the foot and the articulation on the inner side of the foot. This arrangement also has the advantage that the shoe provides protection against pronation injuries as well as supination injuries. It has also been shown that the diagonal position of the straight connecting lines between the two articulations which is effected, according to the invention, toward the front on the outside and toward the rear on the inside facilitates the natural rolling motion of the foot.

In two-piece shoes, the invention is preferably provided at the inner shoe in order to bring the reinforcement as close as possible to the foot and to exclude any separate movements of the foot within the shoe. Examples of two-piece or two-shell shoes with the reinforcement, according to the invention, at the inner shoe include snowboard shoes, mountain shoes, ski shoes, etc.

However, the reinforcement according to the invention can also be used in one-piece shoes such as cross-country shoes, trek shoes, paragliding shoes, cross-country walking shoes, orthopedic shoes, and basketball shoes.

Finally, it is also possible under certain conditions to use the reinforcement according to the invention at the outer shoe of two-piece or two-shell shoes, primarily on closely fitting outer shoes. The diagonal positioning, according to the invention, of the straight connecting lines can be advantageous even in two-shell shoes with hard outer shells (ski shoe) in which supination problems do not occur, since this diagonal positioning facilitates the natural rolling motion of the foot.

In order to prevent collisions between the malleoli and the articulations of the shoe and to improve the mobility of the shoe during normal movement patterns, it is proposed that the articulation on the outer side of the foot is arranged so as to be offset in the downward direction relative to the outer malleolus of the upper ankle joint and that the inside articulation is arranged so as to be offset in the downward direction relative to the inner malleolus of the upper ankle joint.

The inversion-eversion movement is limited so as to reliably reduce joint injuries while simultaneously achieving sufficient basic mobility preferably in that the shaft element is connected in an articulated manner with the stirrup element on the inner side of the foot and on the outer side of the foot via an articulation in each instance and the projection of the connecting straight lines between the two articulations on a horizontal plane containing the transverse axis of the shoe which extends vertically to the longitudinal direction of the shoe and the transverse axis of the shoe enclose an angle of 10° to 30°, preferably approximately 20°.

In a further development of the invention, the shaft element being connected in an articulated manner with the stirrup element on the inner side of the foot and on the outer side of the foot via an articulation in each instance, the projection of the connecting straight lines between the two articulations on a vertical plane containing the transverse axis of the shoe which extends vertically to the longitudinal direction of the shoe and the transverse axis of the shoe enclose an angle of 5° to 15°, preferably approximately 10°.

It has been shown that such an inclination of the connecting straight lines results in a shoe affording a high degree of walking comfort while also providing protection against joint injuries.

Collisions between the malleoli and parts of the articulations on the outer side of the foot and on the inner side of the foot or with the upper ends of the stirrup element are prevented in that the articulation on the inner side of the foot and/or the articulation on the outer side of the foot is/are arranged approximately halfway vertically between the position of the outer malleolus or the position of the inner malleolus of the upper ankle joint and the top of the insole.

There are many possible constructions of the stirrup element and sleeve element. In a preferable construction, the sleeve element has a sleeve, which surrounds the calf and can preferably be closed by a closing element, and a connection part, preferably in the form of a tongue, between the sleeve and the respective articulation, this connection part being rigid against traction. The tongue thus serves for the transmission of tractive forces relieving the loading of the ankle.

In a particularly preferred construction, the tongue and the stirrup element are constructed so as to be rigid against compression. In this way, the forces relieving the loading of the ankle can be transmitted as tractive forces and compressive forces at the outer side of the foot and the inner side of the foot between the sole of the foot and the calf.

In a particularly preferable manner, the tongue which is formed of leather or the like flexible material is reinforced by a plastic plate. The sleeve element can accordingly be formed in its entirety of material with good wearing comfort and good flexibility, in particular leather, with local reinforcement of the tongue by means of the plastic plate in order to obtain the desired rigidity against compression.

The stirrup element can be constructed so as to connect the two articulations and, if appropriate, as a separate stirrup. However, it is also possible to integrate the stirrup element with a sole, especially when the articulations are provided at the outer shoe. In a one-piece shoe or in case of an articulation at the outer shell of a two-piece shoe, the rear heel shell which is provided from the start and which is generally closed at the back is preferably raised at the sides up to the articulations. This provides adequate stability with low manufacturing costs.

In addition to or independently from the steps described above for protecting the wearer of the shoe from injury to the malleoli, at least one of the two articulations is constructed with a substantially vertical articulation play.

More extensive supinating or pronating movements are made possible initially without hindrance, but only to the limit of the articulation play. When the limit is reached, the forces are directed via the respective articulation from the sole of the foot to the calf with corresponding relief of the ankle joints and ligaments.

There are many possible constructions of the articulation or articulations. For example, the stirrup element can be connected with the sleeve element to form the articulation via an articulated pin element which engages in a recess, preferably a hole or, where appropriate, in an elongated hole for vertical articulation play, in the stirrup element and/or in the sleeve element. But at least one articulation can also be formed by means of a material reduction or the like. A further possibility consists in that at least one articulation is formed by a bellows portion or the like.

In particular, the construction of the articulation or articulations by means of a material reduction or the like, e.g., in the form of a film joint, or by means of a bellows portion or the like makes it possible to construct the sleeve element and the stirrup element in one piece. This reduces manufacturing costs for the shoe according to the invention. The respective articulation also remains functional when soiled.

If at least one articulation is formed by means of a bellows portion or the like, the parts of the bellows portion which connect the folds of the bellows portion preferably extend substantially in the longitudinal direction of the shoe and widen toward the rear or toward the front. In this way, the articulation on the inner side of the foot and the articulation on the outer side of the foot are sufficiently localized at the location according to the invention relative to the outer and inner malleolus of the upper ankle joint while ensuring a sufficient rigidity against traction in the articulated connection between the sleeve element and the stirrup element and, as the case may be, after an initial lengthening of the respective bellows portion within defined limits, that is, after vertical articulation play.

The sleeve element can be removable with respect to the stirrup element. In this respect, it is particularly preferable to provide at least two different sleeve elements, particularly with different dimensions especially in the vertical direction, these sleeve elements being connectable with the stirrup element optionally for adapting the shoe to the anatomy of the wearer and/or to adapt the shoe to the intended use. As a result of this step, only a limited number of shoe variants need be manufactured, thus reducing manufacturing costs. The wearer can also adapt the shoe to its intended use when required so that the shoe has a greater useful value for the wearer. It is particularly advisable that the sleeve element be removable, as was mentioned above, and that a plurality of different sleeve elements be provided if the reinforcement according to the invention is provided at the outer shell of a two-shell shoe or at a single-shell shoe.

The sleeve element can be vertically adjustable with respect to the stirrup element. This step also enables the shoe to be adapted to the anatomy of the wearer and/or to the intended use, resulting in the advantages mentioned above.

The reinforcement, according to the invention, for ankle joint stabilization which is described in the preceding can also be advantageously used in connection with an orthopedic stocking or the like textile support fabrics. The frictional engagement between the plantar side of the foot and the stirrup which is required for the desired stabilizing effect is ensured when necessary, that is, when walking, since the foot then presses on the stirrup with instantaneously high force due to the sudden braking of the foot and the body resulting in a temporary frictional engagement.

Consequently, for the sake of simplicity, the stirrup can also be formed by a strip which is rigid against traction and the sleeve element can likewise be formed by a closing strap engaging around the calf and a connecting part, preferably in the form of a tongue, on the inner side and outer side of the foot which is rigid against traction.

The invention is explained in the following with reference to a preferred embodiment example shown in the drawings.

FIG. 8a is a cross-sectional view through a bellows portion, shown in FIG. 7, forming the articulation on the outer side of the foot along lines 8a—8a.

Figure 1:
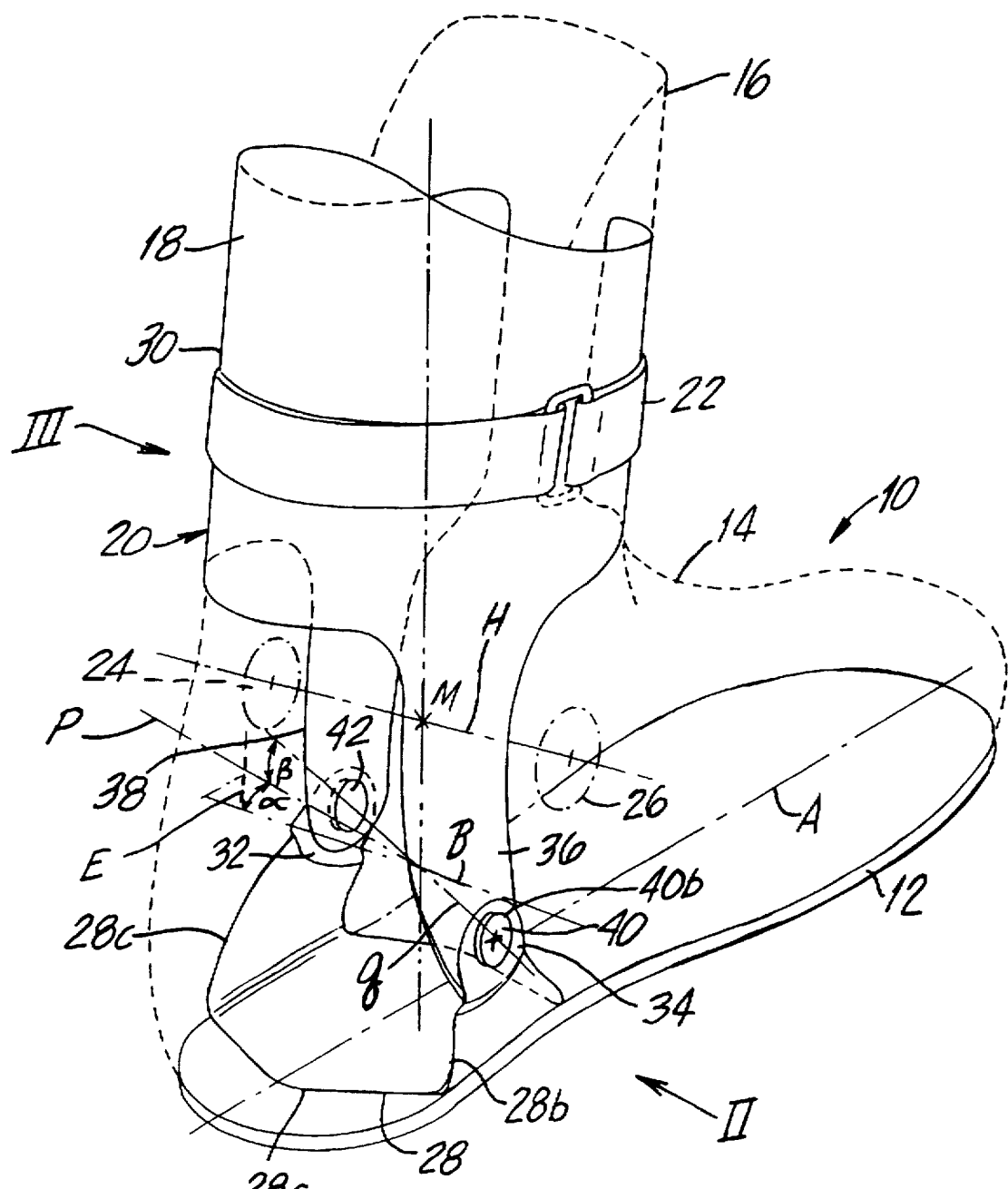
FIG. 1 shows a perspective view of an inner shoe (the outer contour is shown in dashed lines) for a two-piece snowboard shoe with a reinforcement according to the invention.
Figure 2:
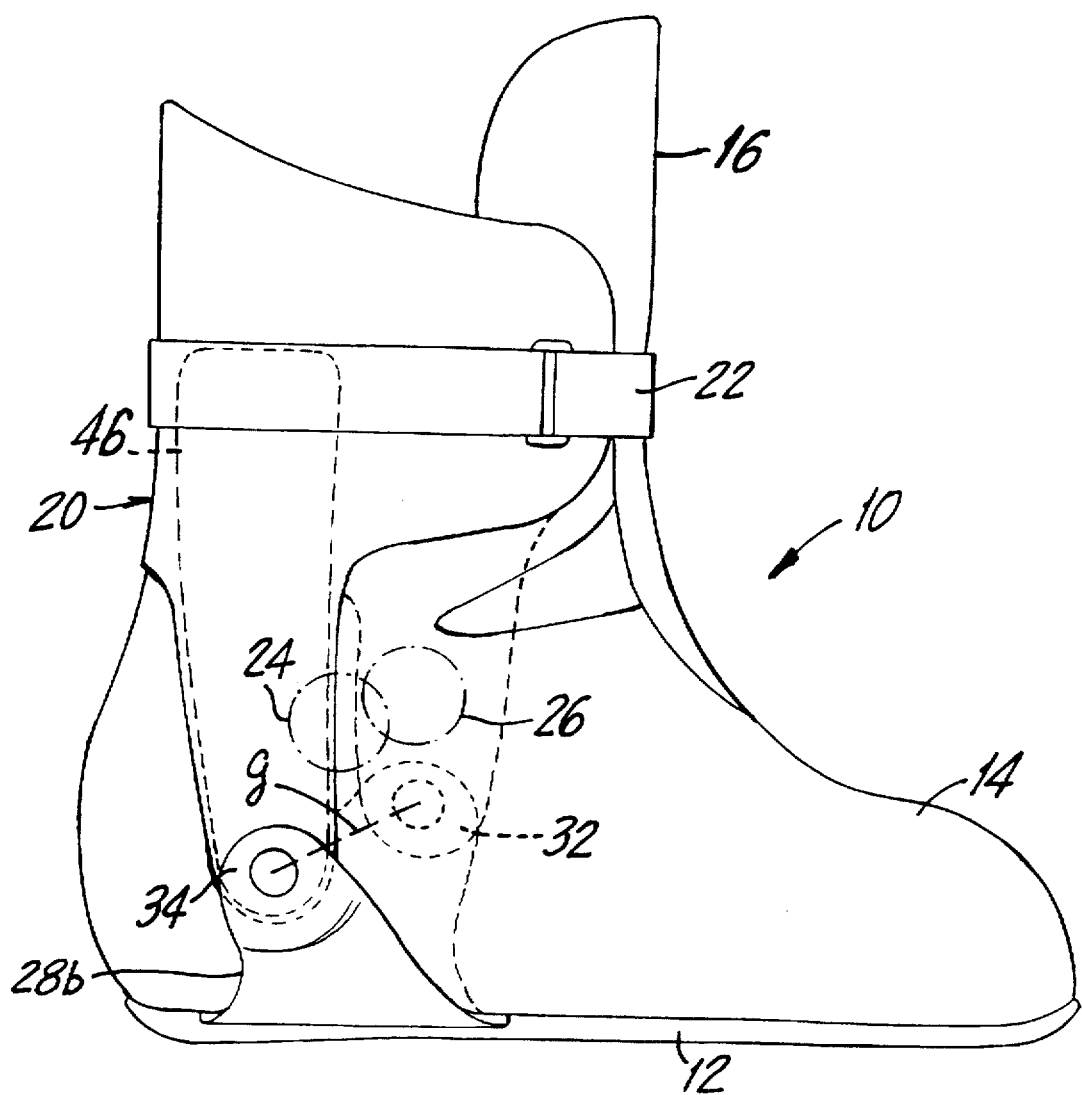
FIG. 2 is a medial view of the inner shoe according to FIG. 1 (viewing direction II in FIG. 1)
Figure 3:
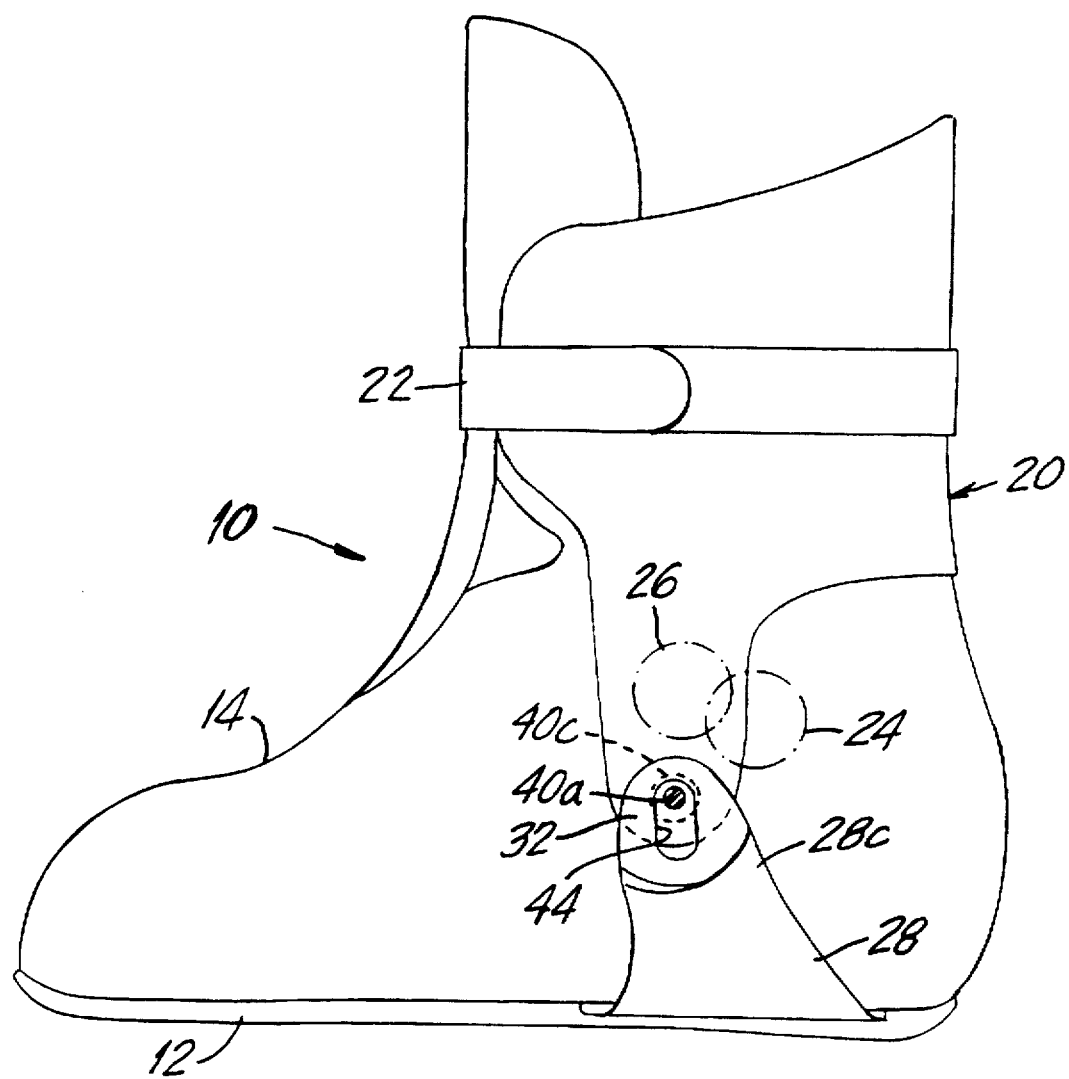
FIG. 3 is a lateral view of the inner shoe according to FIGS. 1 and 2 (viewing direction III in FIG. 1)

The inner shoe 10 which is shown in a simplified manner in FIGS. 1 to 3 and is formed of a sole 12 and upper 14, including the tongue 16, is provided with a sleeve 18 as part of a reinforcement which is designated in its entirety by 20. The sleeve 18 can be closed by a closing element in the form of a closing strap 22 around the calf of the wearer of the shoe above the outer and inner malleolus (indicated in the drawings by a circle 24 and 26 respectively). A hook-and-loop fastener strap, generally known as VELCRO® strap, can be used.

The reinforcement 20 mentioned above is formed by a stirrup element 28 which encloses the foot below the two ankle joints and by a sleeve element 30 which comprises the sleeve 18, these two elements 28 and 30 being connected via an articulation 32 on the outer side of the foot and an articulation 34 on the inner side of the foot.

In the embodiment example shown in the drawing, the stirrup element 28 is constructed as a separate, substantially U-shaped part in cross section vertical to the longitudinal direction A of the shoe. As is shown in the drawing, the center side 28a of the U shape can be arranged at the upper side of the sole 12 of the inner shoe 10, i.e., directly below the insole, not shown, so that there is some kind of direct contact with the sole of the wearer's foot. The sole 12 is made of solid plastic, for example. The articulations 34 and 32 are formed at the free upper ends of the two side legs 28b and 28c of the U shape which overlap for this purpose with the ends of tongues 36 and 38 which project downward from the sleeve 18 on either side of the inner shoe 10 and form part of the sleeve element 20. The ends of the tongues and the ends of the legs are held together by a hinge pin, preferably in the form of a rivet 40 and 42.

In order to achieve a stop-defined relative movability between the stirrup element 28 and the sleeve element 40, a correspondingly vertical articulation play can be provided in one or, better yet, in both articulations 32 and 34. This can be realized, for example, as is shown in FIG. 3, in that a substantially vertically oriented elongated hole 44 is constructed in the upper end of the respective leg 28b and 28c, this elongated hole 44 being penetrated by the shank 40a of the rivet element 40 (in FIG. 3 the outside head 40b of the rivet element 40 is omitted for the sake of clarity and only the inside head 40c is indicated by the dashed line). As a result of this play, a tilting movement of the sleeve element 30 relative to the stirrup element 28 is defined by a stop so that a supinating movement or pronating movement of the foot relative to the calf is accordingly also defined by a stop to a predetermined extent in order to prevent injury to the malleolus.

Independently from this step, but preferably in addition to it, protection against injury is achieved in that the two articulations 32 and 34 are not aligned with one another in the direction of the transverse axis B of the shoe (vertical to the longitudinal direction A and lying in the horizontal plane E), but rather are offset in the longitudinal direction. The articulation 32 on the outer side of the foot (lateral articulation) is offset toward the front in the longitudinal direction A and the articulation 34 on the inner side of the foot (medial articulation) is accordingly offset toward the rear.

According to FIG. 1, the extent of the offset can be described by the angle α enclosed by a projection P of the straight connecting lines G between the two articulations 32 and 34 on the horizontal plane E containing the transverse axis B and by the transverse axis B.

With reference to the foot of the wearer of the shoe, the offset of the articulations 32 and 34 can also be described such that the outer articulation 32 is offset toward the front relative to the center point M of the connecting path H between the two malleoli (circles 24 and 26) and the inner articulation 34 is accordingly offset toward the rear.

The angle α is 10° to 30°, preferably approximately 20°.

Further, the articulations 32 and 34 are offset in the downward direction relative to the malleoli (circles 24 and 26) by up to half the height. The articulation 34 on the inner side of the foot 34 is lower than the articulation 32 on the outer side of the foot, as is shown especially in FIG. 2. The angle of inclination of the straight connecting lines G relative to the horizontal plane E is designated by β in FIG. 1. This angle equals 5° to 15°, preferably approximately 10°.

As a result of the spatial orientation of the articulations 32 and 34, the ankle of the wearer of the shoe is effectively protected against pronation and supination injuries. At the same time, sufficient mobility is ensured.

As a result of the respective offsetting of the articulations 32 and 34 toward the front and rear corresponding to angle α, the tongue 38, articulation 32 and side leg 28c are increasingly relieved of tractive loading with increasing supination or inversion. This is due to the fact that the foot is increasingly swiveled about the Henke axis in the course of the supinating or inverting movement. This axis is orientated opposite to the straight connecting lines G between the two articulations 32 and 34, that is, laterally from the rear and medially toward the front. Accordingly, the articulation 32 is increasingly under tension and the articulation 34 is increasingly under pressure and inhibits further supinating or inverting movement.

The anterior talofibular ligament, which is particularly at risk, passes in front of the outer malleolus (circle 24) as do the tongue 38, articulation 32 and side leg 28c, so that this ligament is protected from excessive pulling directly by the reinforcement according to the invention.

During pronation and eversion, on the other hand, the articulation 32 is under pressure and the articulation 34 is under tension with a corresponding limiting of the loading of the ankle. There is already effective protection against injury when the reinforcement is constructed only for transmitting tractive forces between the sole of the foot and the calf via the two articulations.

However, a further improvement consists in that compressive forces can also be absorbed and transmitted as a result of the reinforcement on the corresponding side, the sleeve element 30 being reinforced for this purpose. If it is desired for reasons pertaining to the wearer's physiology to avoid such a sleeve shell which is rigid against pressure, a separate reinforcing element in the form of a plastic plate 46 can be used as is shown in FIG. 2. This reinforcing element is sewed to the corresponding tongue 36 or 38 as a base, for example, or is inserted into a suitably dimensioned pocket of the sleeve element. The plastic plate 46 reaches from the respective articulation 34 to the closing strap 22 in order to transmit the compressive forces. Since the articulation 34 or 32 itself (possibly, as the case may be, as far as the articulation play mentioned in the preceding) and the adjoining side legs 28b and 28c are also constructed so as to be rigid against pressure, the compressive forces between the sole of the foot and the upper portion of the leg can be transmitted via the reinforcement so as to bypass the malleoli.

The inner shoe described above is characterized by highly effective protection against injury accompanied by sufficient mobility. The reinforcement according to the invention can be realized without substantial expenditure on materials and production.

Figure 4:
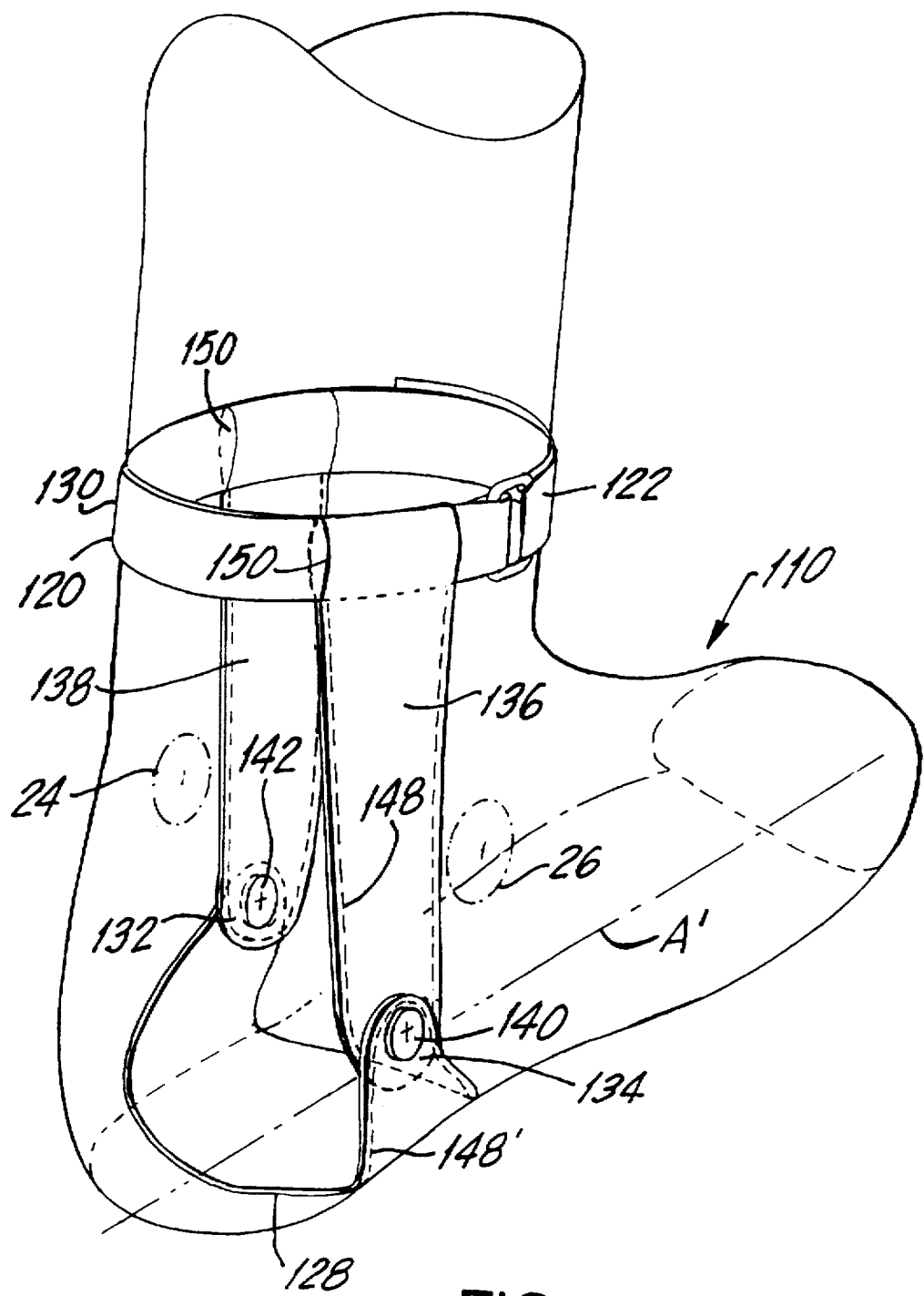
FIG. 4 is a perspective view of an orthopedic stocking with reinforcement according to the invention.

The use of the reinforcement according to the invention in an orthopedic stocking is shown in FIG. 4. The orthopedic stocking 110, which has an opening for the toes in this example, is provided with a reinforcement 120. The reinforcement 120 is formed of a sleeve element 130, the articulation 134 on the inner side of the foot, the articulation 132 on the outer side of the foot, and the stirrup element 128. The sleeve element 130 is formed of a closing strap 122 which is rigid against traction and tongues 136 and 138 which are rigid against traction. The tongues 136 and 138, which can be formed of straps which are rigid against traction, have loops 150 at their upper end through which the closing strap 122 is guided. This closing strap 122 can be a VELCRO ® fastener. The tongues 136 and 138 are sewed together with the orthopedic stocking 110. The corresponding seams 148 are shown in dashed lines. The tongues 136 and 138 are advisably sewn to the outer side of the actual stocking. The closing strap 122 engages around the calf of the wearer above the outer and inner malleolus (indicated by a circle 24 and 26). The stirrup element 128 which engages around the foot below the two ankle joints can likewise be constructed as a strap which is rigid against traction and which is sewn to the outer side of the stocking 110 (seam 148'). Together with the lower end of the respective tongue 136 and 138, the free upper ends of the stirrup element 128 form articulations 132 and 134 in that the stirrup element 128 and the lower ends of the tongues 136 and 138 overlap. The upper ends of the stirrup element 128 and the lower ends of the tongues 136 and 138 are preferably held together in an articulated manner by means of a rivet element 140 and 142.

The two articulations 132 and 134 are offset relative to one another in the longitudinal direction of the stocking in exactly the same way as in the reinforcement of an inner shoe, according to the invention, which was described with reference to FIGS. 1 to 3. The articulation 132 on the outer side of the foot (lateral articulation) is offset toward the front in the longitudinal direction A' and the articulation 134 on the inner side of the foot (medial articulation) is accordingly offset toward the rear. With reference to the wearer's foot, the outer articulation 132 is offset toward the front relative to the center of the connecting path between the two malleoli (circles 24 and 26) and the inner articulation 134 is accordingly offset toward the rear relative to the center of the connecting path.

Further, the articulations 132 and 134 are offset in a downward direction relative to the malleoli (circles 24 and 26) roughly to half of the height. The articulation 134 on the inner side of the foot lies lower down than the articulation 132 on the outer side of the foot.

As in the inner shoe according to FIGS. 1 to 3, the offset of the articulations 132 and 134 relative to the malleoli (circles 24 and 26) or relative to one another can be described by an angle α and an angle β (the angles are not shown in FIG. 4). The angle α describing the offset in the longitudinal direction A' is 10° to 30°, preferably approximately 20°. The angle β which describes the relative vertical offsetting of the articulations 132 and 134 is 5° to 15°, preferably approximately 10°.

As a result of the spatial orientation of the articulations 132 and 134, the wearer of the stocking is effectively protected against pronation and supination injuries to the ankle, since the transmission of tractive forces between the sole of the foot and the calf is sufficient for such protection. Adequate mobility is ensured at the same time.

The orthopedic stocking described above is characterized by a high degree of protection against injury and high therapeutic effectiveness in stabilizing the ankle joints accompanied by sufficient mobility. The reinforcement according to the invention can be realized without substantial expenditure on materials and production.

Additional embodiment forms of a shoe according to the invention which substantially corresponds in its essential design to the inner shoe according to the invention which is shown in FIGS. 1 to 3 are described in the following with reference to FIGS. 5 to 9. Structural component parts which correspond with respect to function to those of the first embodiment form according to FIGS. 1 to 3 are provided with the same reference numbers increased by 100. Only the differences between the embodiment forms will be discussed in the following. In other respects, reference is had to the preceding description of the other embodiment forms.

Figure 5B:
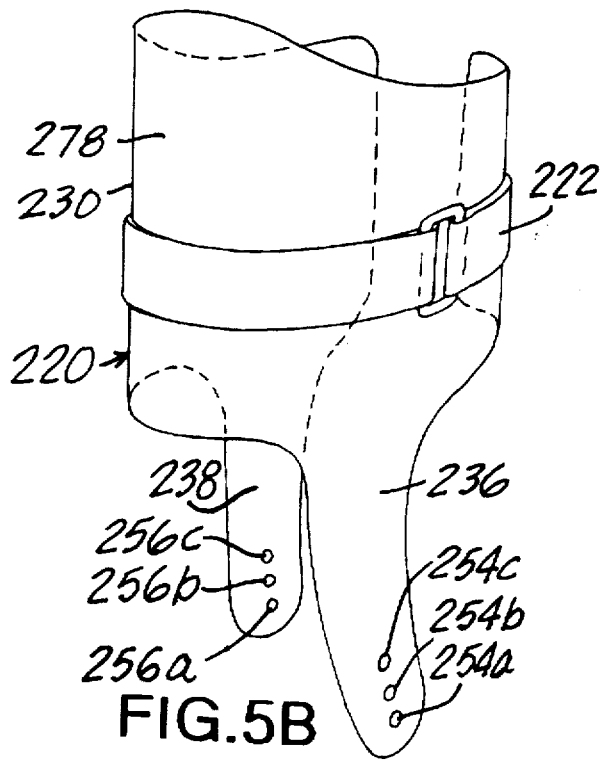
FIG. 5b is a perspective view of a sleeve element of the another embodiment form of a shoe according to the invention corresponding to the inner shoe shown in FIG. 1.

FIG. 5b shows a shoe according to the invention in which the sleeve element 230, including the sleeve 218 and the tongues 236 and 238, can be removed from the stirrup element 228. For this purpose, the inner rivet element 240 and the outer rivet element 242 can be removed from and then replaced in the holes 250 and 252 in the respective side legs 228b and 228c of the stirrup element 228 and the hole in the inner tongue 236 and outer tongue 238, these holes being used to form the articulation. The tongues 236 and 238 have three holes 254a, b, c and 256a, b, c, respectively, which are arranged one above so as to allow the sleeve element 230 to be adjusted in a simple manner with respect to the stirrup element 228.

The rivet elements 240 and 242 have a shank 240a and 242a, an outer head 240b and 242b, and an inner head 240c and 242c, respectively. The inner head 240c and 242c has a substantially smaller diameter than the outer head and is so dimensioned that it can be guided through the respective hole in the stirrup element 228 and into the respective hole in the inner and outer tongue 236 and 238, respectively, the inner head being compressed in a resilient manner and the respective hole being widened in a resilient manner for this purpose, in order to produce the articulated connection of the sleeve element 230 with the stirrup element 228 or to disconnect this articulated connection. The connection between the stirrup element and the sleeve element is prevented from coming undone accidentally in that the rivet head 240c and 242c catches in the inner side of the shoe so that a force must be applied in order to undo the connection.

Figure 5C:
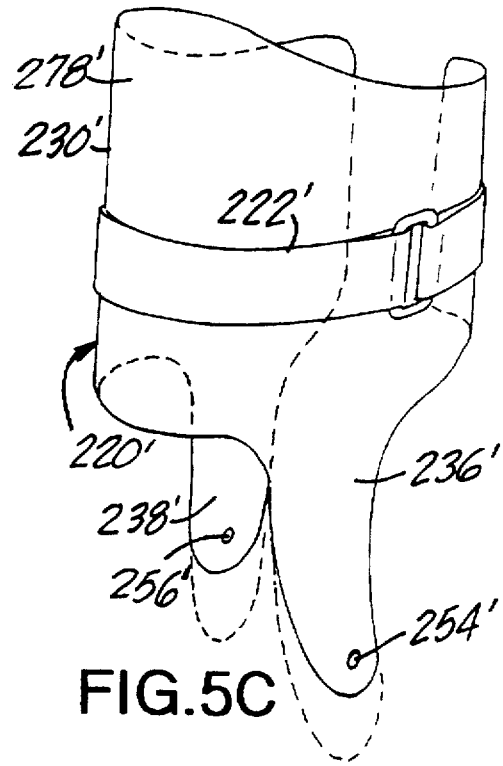
FIG. 5c is a perspective view of another embodiment of the sleeve element of the another embodiment form of a shoe according to the invention corresponding to the inner shoe shown in FIG. 1.
Figure 5A:
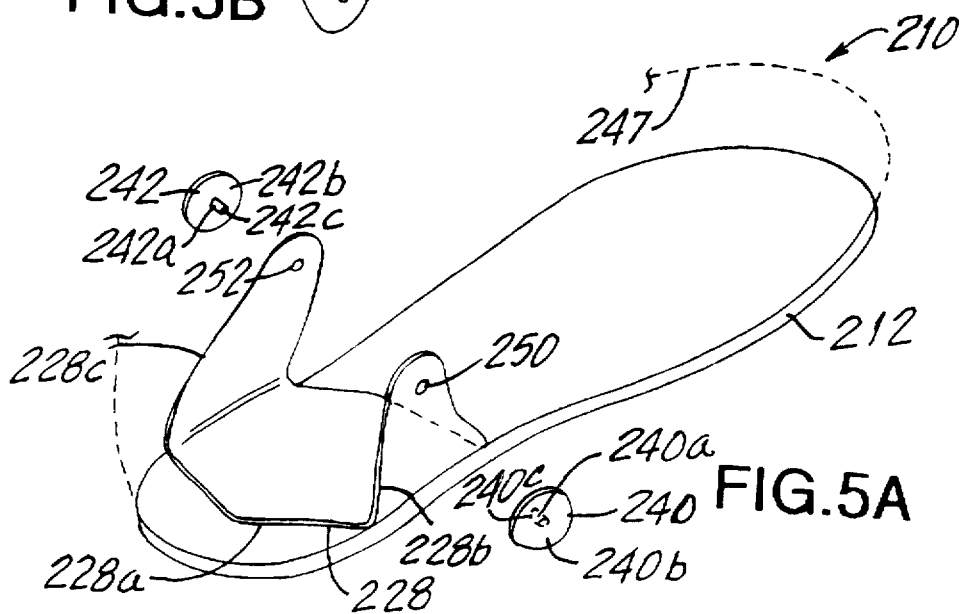
FIG. 5a is a perspective of the sole view of another embodiment form of a shoe according to the invention corresponding to the inner shoe shown in FIG. 1.

In order to optimally adapt the shoe to the anatomy of the wearer or to the intended use of the shoe, a plurality of upper shoe parts, including the sleeve element, can also be provided, the upper parts having, in particular, different dimensions, e.g., different lengths of the tongues for adapting height. FIG. 5c shows a sleeve element 230' of this kind with tongues 236' and 238' which are shorter than the tongues 236 and 238 of the sleeve element 230, which sleeve element 230' can be connected alternatively with the stirrup element 238 by means of the rivet elements 240 and 242.

Figure 6:
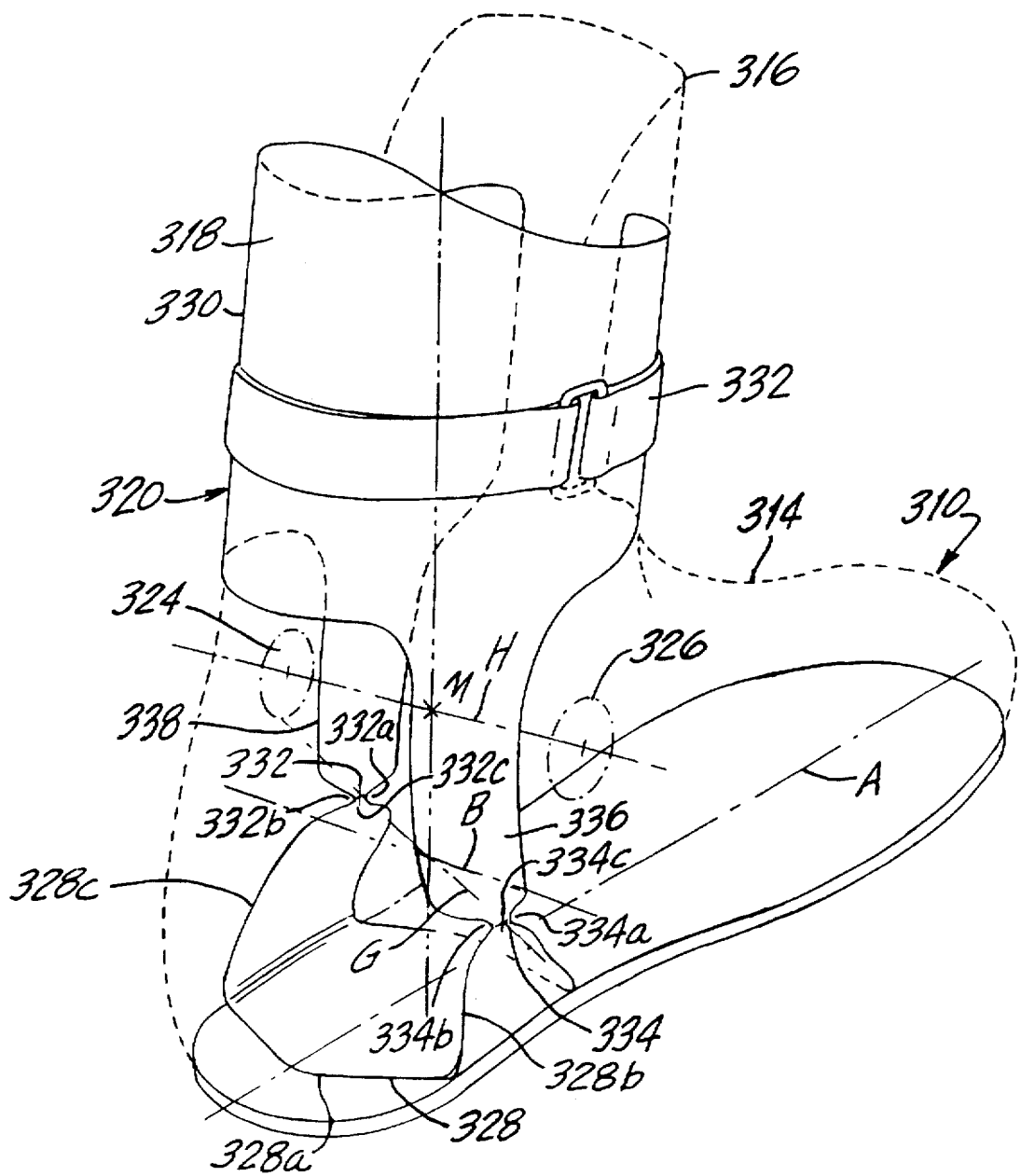
FIG. 6 is a perspective view of another embodiment form of the shoe according to the invention corresponding to the inner shoe shown in FIG. 1.

Another embodiment of the shoe according to the invention is shown in FIG. 6. In this case, the reinforcement 320 is formed in one piece from the sleeve element 330 and stirrup element 328. The articulation 334 on the inner side of the foot and the articulation 332 on the outer side of the foot are formed by a reduction of material in each instance. Each side leg 328b and 328c of the stirrup element 328 is accordingly a part of the respective tongue 336 and 338. In order to form the articulation, the width of the tongue 336 and 338 in the longitudinal direction of the shoe is appreciably reduced in the region of the respective articulation so that a front notch 334a and 332a and a rear notch 334b and 332b are formed. The web 334c and 332c remaining between the upper portion of the tongue 336 and 338 and the side leg 328b and 338c is flexible and consequently forms an articulated connection between the sleeve element 330 and the stirrup element 328. The web 334c and 332c can be reinforced by a suitable bendable reinforcing material, e.g., a wire or the like, in order to withstand particularly high loading.

Figure 7:
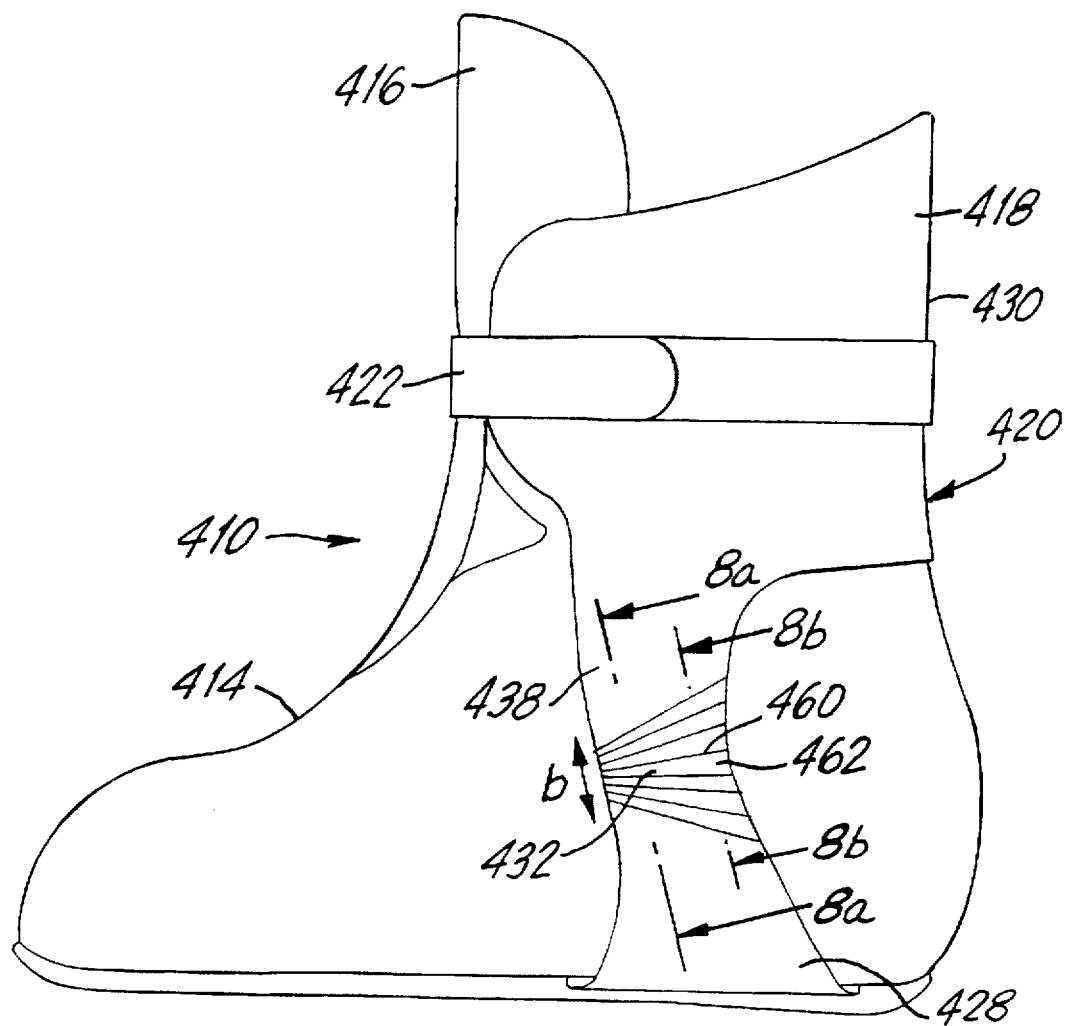
FIG. 7 is a lateral view of another embodiment form of the shoe according to the invention corresponding to the view shown in FIG. 3.

FIGS. 7 and 8 show another embodiment form of a shoe according to the invention. The articulation 432 on the outer side of the foot and the articulation, not shown, on the inner side of the foot are formed by an accordion-like portion referred to as a bellows portion. The bellows portions can be constructed integral with the stirrup element 428 and the sleeve element 430 or can also be constructed as separate parts.

Figure 8A:
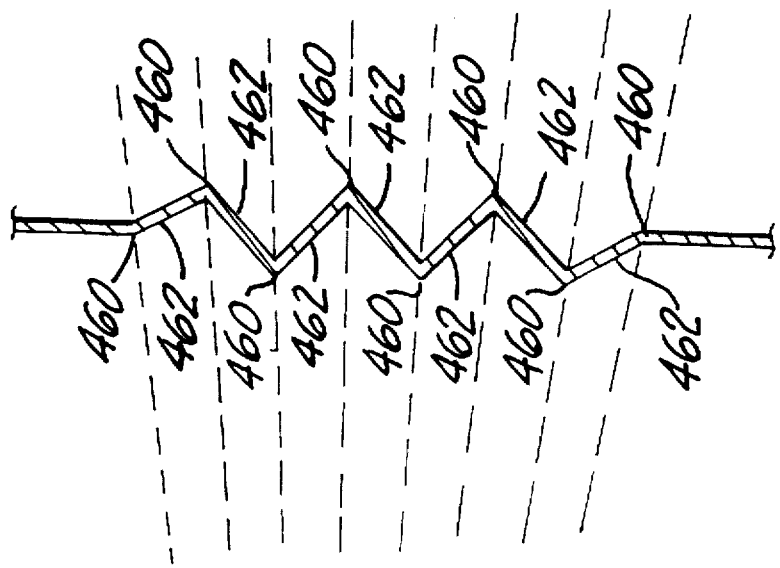
Figure 8B:
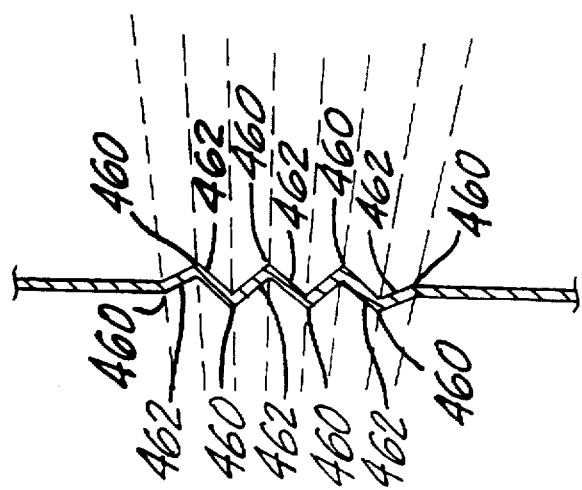
FIG. 8b is a cross-sectional view through a bellows portion, shown in FIG. 7, forming the articulation on the outside of the foot along lines 8b—8b.

The zigzag shape of the bellows portions which is shown in FIGS. 8a and 8b in particular makes it possible for the bellows portion to be expanded and compressed in a resilient manner in the vertical direction. A rotating or swiveling movement of the sleeve element 430 relative to the stirrup element 428 is made possible in that, e.g., the bellows portions are compressed in a front region (lying closer to the toes) and are expanded in a rear region (lying closer to the heel) and vice versa. Thus the bellows portions carry out the articulating function essential to the invention.

An inherent articulation play in the vertical direction is provided in principle owing to the extensibility of the bellows portions.

The parts 462 of the respective bellows portion connecting the folds 460 of the bellows portion extend substantially in the longitudinal direction of the shoe and widen downward resulting in a localization of the articulation point in the front region of the respective bellows portion. As a result of the construction mentioned above, the bellows portion can be expanded or compressed more readily in the rear region than in the front. The distance between the sleeve element and stirrup element during a rotating movement will therefore change less in the front region of the respective bellows portion than in the rear region of the bellows portion. The articulation point is consequently localized more in the front region of the bellows portion.

In a construction of the bellows portions according to FIG. 7—for a given overall resistance to pulling of the bellows portion in its entirety with respect to a lengthening—the resistance of the bellows portions to a rotating movement or swiveling movement between the sleeve element and stirrup element is reduced (given the same overall resistance to pulling) compared with bellows portions having parts of constant width.

The articulation play in the vertical direction is dependent on the vertical dimensioning b of the bellows portion and on the width of the parts 462 at the front edge of the reinforcement according to the invention. In the limiting case where b and accordingly the width of the parts 462 at this location approaches zero, that is, where the folds 460 converge at one point, there is no longer any vertical articulation play and the articulation point coincides with this point in which the folds 460 converge. In this case the articulation point of the articulation formed by the bellows portion is exactly localized.

There is no such localization of the articulation point in the embodiment example shown in FIG. 7, although the articulation point is confined to a relatively small surface. However, this does not impair the protective function according to the invention, since the foot movement, considered purely physiologically, is also not characterized by a stationary axis. The position of the physiological axis of rotation of the foot changes according to the degree of flexion and thus passes over a small surface area on the dorsal surface of the foot. Consequently, it is sufficient if the articulation points of the bellows portions are localized substantially in accordance with said surface area. Thus the articulation axis of the shoe can change to a certain degree during the flexing movement without impairing comfort or undermining the protective function.

Figure 9:
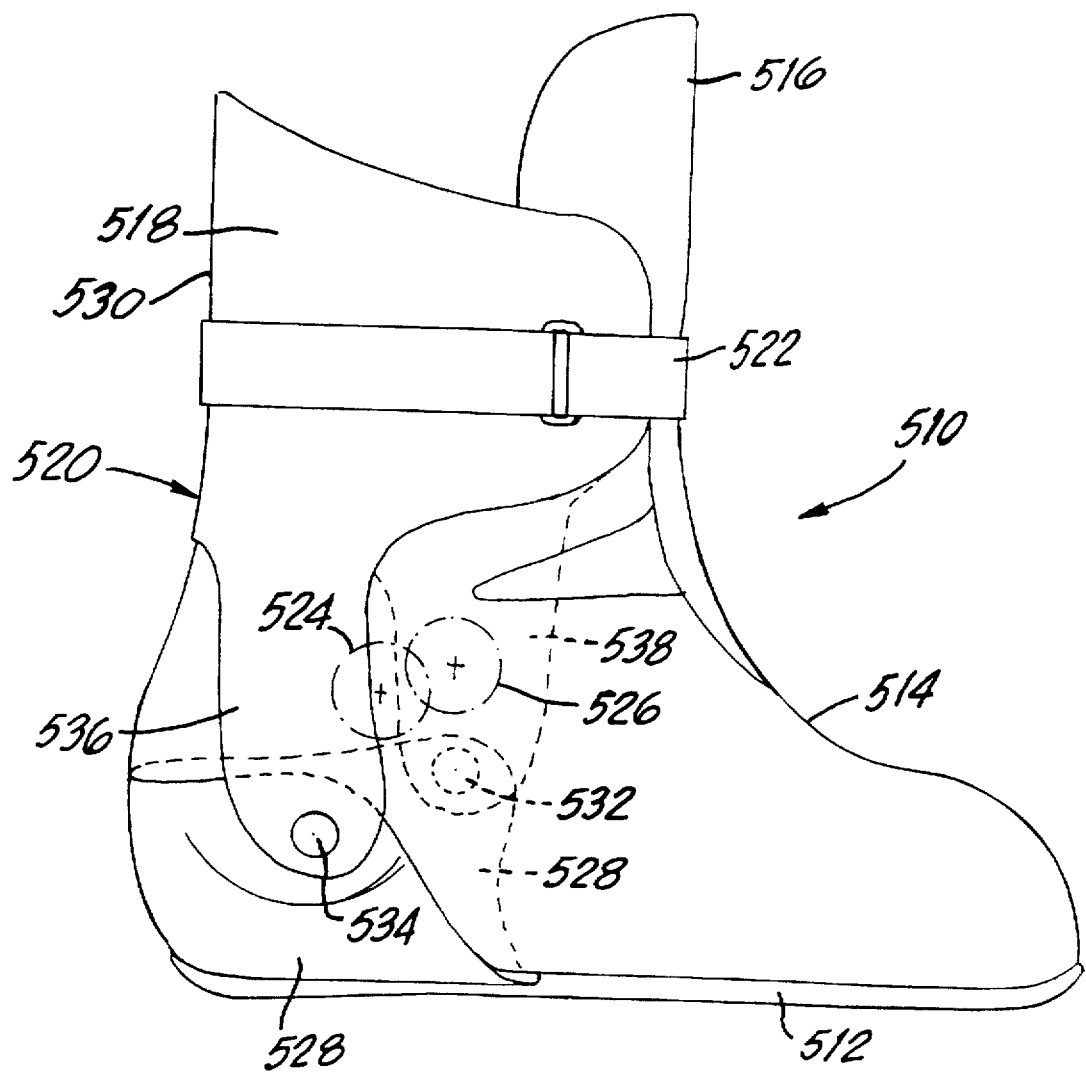
FIG. 9 is an elevational view of another embodiment of a shoe according to the present invention, substantially corresponds to the inner shoe shown in FIG. 1, with a viewing direction corresponding to viewing direction 11 in FIG. 1.

FIG. 9 shows an elevational view of another embodiment of a shoe according to the present invention, substantially corresponds to the inner shoe according to the invention shown in FIGS. 1–3 (see in particular FIG. 2). In the embodiment of a shoe shown in FIG. 9, instead of the stirrup element 28 (with components 28a, 28b, 28c) of the embodiment of FIGS. 1–3, the shoe 510 has a rear heel shell 528 closed at the back. To serve as a stirrup element, the rear heel shell 528 is raised at the sides up to the articulations which connect the rear heel shell 528 with the tongues 536 and 538 of the reinforcement 520. Other details of the shoe shown in FIG. 9, namely, sole 512, an upper 514 with a tongue 516, a sleeve 518, a closing strap 522 which is located above the outer and inner malleolus 524, 526, a sleeve element 530, and outer and inner articulations 532 and 534 are similar to those of FIGS. 1–3.

In conclusion, in a shoe, in particular a sports shoe, with a reinforcement which partially or entirely encloses the foot below the ankle joints and which extends above the upper ankle joint on one or both sides of the foot, wherein the reinforcement has a stirrup element which at least partially surrounds the foot below the ankle joints and a sleeve element which at least partially surrounds the calf above the upper ankle joint, and wherein the sleeve element is connected with the stirrup element on the inner side of the foot and/or on the outer side of the foot via an articulation in order to transmit at least tractive forces between the stirrup element and the sleeve element, it is proposed that the articulation on the outer side of the foot is arranged so as to be offset toward the front in the longitudinal direction of the shoe relative to a center position between the outer malleolus and the inner malleolus of the upper ankle joint and that the articulation on the inner side of the foot is arranged so as to be offset toward the rear in the longitudinal direction of the shoe relative to the center position. In this way, reliable protection against injury is achieved with sufficient mobility. The reinforcement according to the invention can also be used in connection with an orthopedic stocking or the like textile support fabrics for stabilization of the ankle joints.

I claim:
1. A shoe, comprising:
a reinforcement (20) for at least partially enclosing a foot of a shoe wearer below ankle joints of the foot and for extending above an upper ankle joint of the foot, the reinforcement (20) having a stirrup element (28) for at least partially surrounding the foot below the ankle joints and a sleeve element (30) for at least partially surrounding a calf of the shoe wearer above the upper ankle joint; and
inner side (34) and outer side (32) articulations for connecting the sleeve element (30) with the stirrup element (28) on inner and outer sides of the foot, respectively, for transmitting of at least tractive forces between in the stirrup element (28) and the sleeve element (30), wherein the outer side articulation (32) is offset relative to the inner side articulation (34) toward a front portion of the shoe in a longitudinal direction (A) of the shoe, and
wherein a projection (P) of a straight line (G), which connects the inner and outer side articulations (34; 32), on a horizontal plane (E) forms with a transverse axis (B), which lies in the horizontal plane (E), an angle α of at least 10°.

2. The shoe according to claim 1, wherein the angle between the projection (P) and the transverse axis (B) is between 10° and 30°.

3. The shoe according to claim 1, wherein the angle between the projection (P) and the transverse axis (B) is about 20°.

4. The shoe according to claim 1, wherein the outer articulation (32) is offset relative to a center of an outer malleolus receiving portion of the shoe toward the front portion of the shoe in the longitudinal direction (A) of the shoe.

5. The shoe according to claim 1, wherein the inner articulation (34) is offset relative to a center of an inner malleolus receiving portion of the shoe toward a rear portion of the shoe in the longitudinal direction (A) of the shoe.

6. The shoe according to claim 1, wherein the outer articulation (32) is offset relative to a center of an outer malleolus receiving portion of the shoe toward the front portion of the shoe in the longitudinal direction (A) of the shoe, and the inner articulation (34) is offset relative to a center of an inner malleolus receiving portion of the shoe toward the rear portion of the shoe in the longitudinal direction (A) of the shoe.

7. The shoe according to claim 1, wherein the outer articulation (32) is offset relative to a center position (M) between a center of an outer malleolus receiving portion of the shoe and a center of an inner malleolus receiving portion of the shoe toward the front portion of the shoe in the longitudinal direction (A) of the shoe.

8. The shoe according to claim 1, wherein the inner articulation (34) is offset relative to a center position (M) between a center of an outer malleolus receiving portion of the shoe and a center of an inner malleolus receiving portion of the shoe toward a rear portion of the shoe in the longitudinal direction (A) of the shoe.

9. The shoe according to claim 1, wherein the outer articulation (32) is offset relative to a center position (M) between a center of an outer malleolus receiving portion of the shoe and a center of an inner malleolus receiving portion of the shoe toward the front portion of the shoe in the longitudinal direction (A) of the shoe, and the inner articulation (34) is offset relative to the center position (M) toward a rear portion of the shoe in the longitudinal direction (A) of the shoe.

10. The shoe according to claim 1, wherein the outer side articulation (32) is offset in a downward direction relative to a center of an outer malleolus receiving portion of the shoe, and the inner side articulation (34) is offset in a downward direction relative to a center of an inner malleolus receiving portion of the shoe.

11. The shoe according to claim 1, wherein the outer (32) and inner (34) side articulations are located approximately halfway vertically between centers of outer and inner malleolus receiving portions of the shoe, respectively, and a top of an insole of the shoe.

12. The shoe according to claim 1, wherein the shoe is formed as a one-piece shoe.

13. Shoe according to claim 1, wherein the shoe is formed as a two-piece shoe.

14. The shoe according to claim 1, wherein the shoe is a two-piece shoe, and wherein the stirrup element (28), the sleeve element (30), and one of the outer and inner articulations (32; 34) are arranged at an outside of an outer shoe of the two-piece shoe.

15. The shoe according to claim 1, wherein the sleeve element (30) forms regions of an upper (14) of the shoe.

16. The shoe according to claim 1, wherein the sleeve element (30) has a sleeve (18), which surrounds the calf, and a tension-proof connection part (36; 38) connecting the sleeve (18) with a respective articulation (32; 34).

17. The shoe according to claim 1, wherein the sleeve element (30) has a sleeve (18), which surrounds the calf, and a tension-proof connection part (36; 38) connecting the sleeve (18) with a respective articulation (32; 34), and wherein the connection part (36; 38) is formed as a compression-proof tongue.

18. The shoe according to claim 1, wherein the sleeve element (30) has a sleeve (18), which surrounds the calf, and a tension-proof connection part (36; 38) connecting the sleeve (18) with a respective articulation (32; 34), and wherein the connection part (36; 38) is formed as a tongue made of a flexible material and has a reinforcing plastic plate (46).

19. The shoe according to claim 1, wherein the stirrup element (28) is formed as a stirrup connecting the outer and inner articulations (34; 34).

20. The shoe according to claim 1, wherein the stirrup element (28) is formed as a separate stirrup connecting the outer and inner articulations.

21. The shoe according to claim 1, wherein the stirrup element (28) is integrated with a sole (12).

22. The shoe according to claim 1, wherein a rear heel shell is raised at the outer and inner sides up to the outer and inner articulations (32; 34) to form the stirrup element (28).

23. The shoe according to claim 1, wherein a rear heel shell is closed at the back and is raised at the outer and inner sides up to the outer and inner articulations to form the stirrup element (28).

24. The shoe according to claim 1, wherein the stirrup element (28; 228) is connected with the sleeve element (30; 230; 230') for forming an articulation via an articulated pin element (40; 42; 240; 242) which engages in a recess (250; 252; 254; 256; 254'; 256') in at least one of the stirrup element (28; 228) and the sleeve element (30; 230; 230').

25. The shoe according to claim 1, wherein at least one of outer and inner articulations is formed by reduction of material (332, 334).

26. The shoe according to claim 1, wherein at least one of the outer and inner articulations (32; 34) is formed with a substantially vertical articulation play, and wherein the stirrup element (28) is connected with the sleeve element (30) to form an articulation via a hinge pin element (40; 42) which penetrates an elongate hole (44) in at least one of the stirrup element (28) and the sleeve element (30).

27. The shoe according to claim 1, wherein at least one of the outer and inner articulations is formed by a bellows portion (432).

28. The shoe according to claim 1, wherein at least one of the outer and inner articulations is formed by a bellows portion, and wherein parts (462) of the bellows portion (432), which connect folds (460) of the bellows portion (432), extend substantially in the longitudinal direction of the shoe and widen toward one of a rear and a front of the shoe.

29. The shoe according to claim 1, comprising at least two interchangeable sleeve elements (230; 230') having different dimensions in a vertical direction for adapting the shoe to at least one of an anatomy of the wearer and an intended use.

30. The shoe according to claim 1, wherein the sleeve element (330) and the stirrup element (328) are formed as a one-piece member.

31. The shoe according to claim 1, wherein a projection of the straight line (G) on a vertical plane, in which the transverse axis (B) lies, forms an angle of 5° to 15° with the transverse axis (B), and wherein the outer articulation (32) is offset relative to the inner articulation (34) toward a top portion of the shoe in a vertical direction.

32. The shoe according to claim 1, wherein a projection of the straight line (G) on a vertical plane, in which the transverse axis (B) lies, forms an angle of approximately 10° with the transverse axis (B), and wherein the outer articulation (32) is offset relative to the inner articulation (34) toward a top portion of the shoe in a vertical direction.

33. The shoe according to claim 1, comprising an inner shoe (10), and wherein the stirrup element (28), the sleeve element (30), and one of the outer and inner articulations (32; 34) are arranged at the inner shoe (10).

34. The shoe according to claim 1, comprising an upper (14), and wherein the stirrup element (28), the sleeve element (30), and one of the inner and outer articulations (34; 32) are arranged at an inner side of the upper.

35. The shoe according to claim 1, wherein the shoe comprises a single shoe member, and wherein the stirrup element (28), the sleeve element (30), and one of the outer and inner articulation are arranged at an outer side of the shoe member.

36. The shoe according to claim 1, further comprising means (40, 44, 460, 462) for enabling a substantial vertical play of at least one of the outer and inner articulations (32, 34, 432).

37. The shoe according to claim 1, further comprising means (240, 242, 250, 252) for disconnecting the sleeve element (230; 230') from the stirrup element (228).

38. The shoe according to claim 1, further comprising means (240, 242, 250, 252, 254, 256) for vertically adjusting a vertical position of the sleeve element (230) relative to the stirrup element (228).

39. An orthopedic stocking, comprising:
 a reinforcement (120) for completely enclosing a foot of a stocking wearer below ankle joints of the foot and for extending above an upper ankle joints of the foot, the reinforcement (120) having a stirrup element (128) for surrounding the foot below the ankle joint and a sleeve element (130) for surrounding a calf of the stocking wearer above the upper ankle joint; and
 inner side (134) and outer side (132) articulations for connecting the sleeve element (130) with the stirrup element (128) on inner and outer sides of the foot, respectively, for transmitting of at least tractive forces between the stirrup element (128) and the sleeve element (130),
 wherein the outer side articulation (130) is offset relative to the inner side articulation (134) toward a front portion of the stocking in a longitudinal direction (A), and
 wherein a projection (P) of a straight line (G), which connects the inner and outer side articulations (134; 132), on a horizontal plane (E) forms with a transverse axis (B), which lies in the horizontal plane (E), an angle α of at least 10°.

40. The stocking according to claim 39, wherein the angle between the projection (P) and the transverse axis (B) is between 10° and 30°.

41. The stocking according to claim 39, wherein the angle between the projection (P) and the transverse axis (B) is about 20°.

42. The stocking according to claim 39, wherein the outer articulation (132) is offset relative to a center of an outer malleolus receiving portion of the stocking toward the front portion in the longitudinal direction (A) of the stocking.

43. The stocking according to claim 39, wherein the inner articulation (134) is offset relative to a center of an inner malleolus receiving portion of the stocking toward a rear portion in the longitudinal direction (A) of the stocking.

44. The stocking according to claim 39, wherein the outer articulation (132) is offset relative to a center of an outer malleolus receiving portion of the stocking toward the front portion in the longitudinal direction (A) of the stocking, and the inner articulation (134) is offset relative to a center of an inner malleolus receiving portion of the stocking toward the rear portion of the shoe in the longitudinal direction of the stocking.

45. The stocking according to claim 39, wherein the outer articulation (132) is offset relative to a center position (M) between a center of an outer malleolus receiving portion and a center of an inner malleolus receiving portion of the stocking toward the front portion of the stocking in the longitudinal direction (A) of the stocking.

46. The stocking according to claim 39, wherein the inner articulation (134) is offset relative to a center position (M) between a center of an outer malleolus receiving portion of the stocking and a center of an inner malleolus receiving portion of the stocking toward a rear portion of the stocking in the longitudinal direction (A) of the stocking.

47. The stocking according to claim 39, wherein the outer articulation (132) is offset relative to a center position (M) between a center of an outer malleolus receiving portion of the stocking and a center of an inner malleolus receiving portion of the stocking toward the front portion of the stocking in the longitudinal direction (A) of the stocking and the inner articulation (134) is offset relative to the center position (M) toward a rear portion of the stocking in the longitudinal direction (A) of the stocking.

48. The stocking according to claim 39, wherein the stirrup element (128) is formed by a tension-proof strap.

49. The stocking according to claim 39, wherein the sleeve element (130) is formed by a tension-proof closing strap (122) which engages around a calf of the stocking wearer, and by a tension-proof connection part (136; 138) provided on the inner side and outer side of the foot between the closing strap (122) and a respective articulation (132; 134).

50. The stocking according to claim 39, wherein the sleeve element (130) is formed by a tension-proof closing strap, which engages around the calf of the stocking wearer, and by a tension-proof connection part (136; 138) formed as a tongue provided on the inner side and the outer side of the foot between the closing strap (122) and a respective articulation (132; 134), the tongue being formed by a tension-proof strap.

51. The stocking according to claim 39, wherein the outer side articulation (132) is offset in a downward direction relative to a center of an outer malleolus receiving portion of the stocking, and the inner side articulation (134) is offset in a downward direction relative to a center of an inner malleolus receiving portion of the stocking.

52. The stocking according to claim 39, wherein the inner (134) and outer (132) side articulations are arranged approximately halfway vertically between centers of inner and outer malleolus receiving portions of the stocking, respectively, and a top of an insole of the stocking.

53. The stocking according to claim 39, wherein a projection of the straight line (G) on a vertical plane, in which the transverse axis (B) lies, forms an angle of 5° to 15° with the transverse axis (B), and wherein the outer articulation (32) is offset relative to the inner articulation (34) toward a top portion of the stocking in a vertical direction.

54. The stocking according to claim 53, wherein the angle between the projection and the transverse axis (B) is approximately 10°.

55. A shoe, comprising:
a reinforcement (20) for at least partially enclosing a foot of a shoe wearer below the ankle joints of the foot and for extending above the upper ankle joint of the foot, the reinforcement (20) having a stirrup element (28) for at least partially surrounding the foot below the ankle joints and a sleeve element (30) for at least partially surrounding the calf of the shoe wearer above the upper ankle joint; and
articulation means consisting of an outer-side articulation (32) for connecting the sleeve element (30) with the stirrup element (28) on the outer side of the foot, for transmitting of at least tractive forces between the stirrup element (28) and the sleeve element (30).
wherein the outer side articulation is offset relative to the center of an outer malleolus receiving portion of the shoe toward a front portion of the shoe in a longitudinal direction (A) of the shoe, and
wherein a projection of a straight line G, which connects the outer side articulation (32) and a center position (M) between the center of the outer malleolus receiving portion of the shoe and the center of an inner malleolus receiving portion of the shoe on a horizontal plane forms with a transverse axis (B), which lies in the horizontal plane, an angle α of at least 10°.

56. The shoe according to claim 55, wherein the angle between the projection (H) and the transverse axis (B) is between 10° and 30°.

57. The shoe according to claim 55, wherein the angle between the projection (H) and the transverse axis (B) is about 20°.

58. The shoe according to claim 55, wherein the outer articulation (32) is offset relative to the center position (M) toward a front portion of the shoe.

59. The shoe according to claim 55, wherein the outer side articulation (32) is offset in a downward direction relative to the center of the outer malleolus receiving portion of the shoe.

60. The shoe according to claim 55, wherein the outer side articulation (32) is located approximately halfway vertically between the center of the outer malleolus receiving portion of the shoe and a top of an insole of the shoe.

61. The shoe according to claim 55, wherein the shoe is formed as a two-piece shoe.

62. Shoe according to claim 55, wherein the shoe is formed as a two-piece shoe, and wherein the stirrup element (28), the sleeve element (30), and the outer articulation (32); are arranged at an inner shoe (10).

63. The shoe according to claim 55, wherein the shoe is formed as a two-piece shoe, and wherein the stirrup element (28), the sleeve element (30), and the outer side articulation (32) are arranged at an inner side of an outer shoe.

64. The shoe according to claim 55, wherein the shoe is formed as a two-piece shoe, and wherein the stirrup element (28), the sleeve element (30), and the outer side articulation (32) are arranged at the outside of an outer shoe.

65. The shoe according to claim 55, wherein the shoe is formed as a one-piece shoe, and wherein the stirrup element (28), the sleeve element (30), and the outer side articulation (32) are arranged at an outer side of the shoe.

66. The shoe according to claim 55, wherein the sleeve element (30) forms regions of an upper (14) of the shoe.

67. The shoe according to claim 55, wherein the sleeve element (30) has a sleeve (18), which surrounds the calf, and a tension-proof connection part (38) between the sleeve (18) and the outer articulation (32).

68. The shoe according to claim 55, wherein the sleeve element (30) has a sleeve (18), which surrounds the calf, and a tension-proof connection part (38) connecting the sleeve (18) with the outer articulation (32), and wherein the connection part is formed as a compression-proof tongue.

69. The shoe according to claim 55, wherein the sleeve element (30() has a sleeve (18), which surrounds the calf, and a tension-proof connection part (38) between the sleeve and the outer articulation (32), the connection part being formed as a tongue made of a flexible material and having a reinforcing plastic plate (46).

70. The shoe according to claim 55, wherein the stirrup element (28) is integrated with a sole (12).

71. The shoe according to claim 55, wherein a rear heel shell is raised at the outer side up to the outer articulations (32) to form the stirrup element (28).

72. The shoe according to claim 55, wherein the rear heel shell is closed at the back and is raised at the outer side up to the outer articulation (32) to form the stirrup element (28).

73. The shoe according to claim 55, wherein the stirrup element (28; 228) is connected with the sleeve element (30; 230; 230') for forming an articulation via an articulated pin element (42; 242) which engages in a recess (252; 256; 256'), in at least one of the stirrup element (28; 228) and the sleeve element (30; 230; 230').

74. The shoe according to claim 55, wherein the outer articulation (32) is formed by reduction of material (332).

75. The shoe according to claim 55, wherein the outer articulation is formed with a substantially vertical articulation play, and wherein the stirrup element (28) is connected with the sleeve element (30) to form an articulation via a hinge pin element (42) which penetrates an elongated hole (44) in at least one of the stirrup element (28) and the sleeve element (30).

76. The shoe according to claim 55, wherein the outer articulation (32) is formed by a bellows portion (432).

77. The shoe according to claim 55, wherein the outer articulation is formed by a bellows portion (432), and wherein parts (462) of the bellows portion (432), which connect folds (460) of the bellows portion (432), extend substantially in the longitudinal direction (A) of the shoe and widen toward one of a rear and a front of the shoe.

78. The shoe according to claim 55, comprising at least two interchangeable sleeve elements (230, 230') having different dimensions in a vertical direction for adapting the shoe to at least one of an anatomy of the wearer and an intended use.

79. The shoe according to claim 55, wherein the sleeve element (330) and the stirrup element (328) are formed as a one-piece member.

80. The shoe according to claim 55, wherein the shoe is formed as one-piece shoe.

81. The shoe according to claim 55, further comprising means (40, 44) for enabling a substantial vertical play of the outer articulation (32, 432).

82. The shoe according to claim 55, further comprising means (242, 252) for disconnecting the sleeve element (230, 231) from the stirrup element (228).

83. The shoe according to claim 55, further comprising means (240, 242, 252, 256) for vertically adjusting a vertical position of the sleeve element (230) relative to the stirrup element (228).

* * * * *